United States Patent

Saita et al.

(10) Patent No.: US 9,671,134 B2
(45) Date of Patent: Jun. 6, 2017

(54) VAPOR HEATING IMPLEMENT

(71) Applicant: KAO CORPORATION, Chuo-ku (JP)

(72) Inventors: Yasuto Saita, Yokohama (JP); Takeshi Oka, Funabashi (JP); Yuko Shimada, Sumida-ku (JP)

(73) Assignee: KAO CORPORATION, Chuo-ku (JP)

( * ) Notice: Subject to any disclaimer, the term of this patent is extended or adjusted under 35 U.S.C. 154(b) by 186 days.

(21) Appl. No.: 14/367,536

(22) PCT Filed: Dec. 21, 2012

(86) PCT No.: PCT/JP2012/083311
§ 371 (c)(1),
(2) Date: Jun. 20, 2014

(87) PCT Pub. No.: WO2013/094746
PCT Pub. Date: Jun. 27, 2013

(65) Prior Publication Data
US 2014/0345543 A1  Nov. 27, 2014

(30) Foreign Application Priority Data

Dec. 21, 2011 (JP) .................................. 2011-280595

(51) Int. Cl.
*F24J 1/00* (2006.01)
*A61F 7/03* (2006.01)
(Continued)

(52) U.S. Cl.
CPC ................ *F24J 1/00* (2013.01); *A61F 7/034* (2013.01); *A61F 2007/0003* (2013.01);
(Continued)

(58) Field of Classification Search
CPC .... A61F 7/03; A61F 7/034; A61F 2007/0214; A61F 2007/0225; A61F 2007/0062;
(Continued)

(56) References Cited

U.S. PATENT DOCUMENTS 6,436,128 B1   8/2002 Usui
6,629,964 B1  10/2003 Ono et al.
(Continued)

FOREIGN PATENT DOCUMENTS

CN      1491271 A    4/2004
CN    101820836 A    9/2010
(Continued)

OTHER PUBLICATIONS

Combined Chinese Office Action and Search Report issued Feb. 3, 2015 in Patent Application No. 201280063336.1 (with English language translation and English translation of categories of documents).
(Continued)

*Primary Examiner* — Steven B McAllister
*Assistant Examiner* — Steven Anderson, II
(74) *Attorney, Agent, or Firm* — Oblon, McClelland, Maier & Neustadt, L.L.P.

(57) ABSTRACT

A vapor heating implement satisfies: (A) the content of water in the heating implement is equal to or higher than 40 parts by mass and is equal to or lower than 80 parts by mass for 100 parts by mass of the oxidizable metal; (B) the content of the water-retention agent in the exothermic composition is equal to or higher than 0.3 parts by mass and is equal to or lower than 20 parts by mass for 100 parts by mass of the oxidizable metal; (C) the content of water contained in the exothermic layer (121A) is equal to or higher than 8 parts by mass and is equal to or lower than 45 parts by mass for 100 parts by mass of the oxidizable metal; and (D) the content of water contained in the water-retention sheet (121C) is from 15 to 30 mass % of the maximum water absorption of the water-retention sheet.

19 Claims, 4 Drawing Sheets

(51) Int. Cl.
    *A61F 7/00* (2006.01)
    *A61F 7/02* (2006.01)
(52) U.S. Cl.
    CPC ............ *A61F 2007/0004* (2013.01); *A61F 2007/0062* (2013.01); *A61F 2007/0098* (2013.01); *A61F 2007/022* (2013.01); *A61F 2007/026* (2013.01); *A61F 2007/0214* (2013.01); *A61F 2007/0225* (2013.01); *A61F 2007/0258* (2013.01)
(58) Field of Classification Search
    CPC ...... A61F 2007/0098; A61F 2007/0258; A61F 2007/026; A61F 2007/0004; A61F 2007/022; F24J 1/00
    USPC .......................................................... 122/21
    See application file for complete search history.

(56) References Cited

U.S. PATENT DOCUMENTS

| | | | |
|---|---|---|---|
| 6,863,682 | B2 | 3/2005 | Usui |
| 8,343,203 | B2 | 1/2013 | Ishikawa |
| 2002/0151947 | A1 | 10/2002 | Usui |
| 2004/0035410 | A1* | 2/2004 | Igaki ................ A61F 7/03 126/263.05 |
| 2004/0042965 | A1 | 3/2004 | Usui et al. |
| 2006/0154006 | A1 | 7/2006 | Usui et al. |
| 2006/0276863 | A1* | 12/2006 | Kumamoto ........... A61F 7/034 607/96 |
| 2007/0156213 | A1 | 7/2007 | Friedensohn et al. |
| 2010/0198325 | A1 | 8/2010 | Ishikawa |
| 2010/0241199 | A1 | 9/2010 | Hidaka et al. |
| 2011/0190714 | A1 | 8/2011 | Oda et al. |
| 2013/0125837 | A1 | 5/2013 | Ueno et al. |

FOREIGN PATENT DOCUMENTS

| | | |
|---|---|---|
| EP | 1 147 752 A1 | 10/2001 |
| EP | 2 177 183 A1 | 4/2010 |
| JP | 9-75388 | 3/1997 |
| JP | 2003-129041 | 5/2003 |
| JP | 2004-26904 | 1/2004 |
| JP | 2004-208978 | 7/2004 |
| JP | 2009-39370 | 2/2009 |
| KR | 10-2004-0052207 | 6/2004 |
| KR | 10-2011-0091850 | 8/2011 |
| TW | 495547 B | 7/2002 |
| TW | 200414897 A | 8/2004 |
| TW | 200624137 A | 7/2006 |
| WO | WO 2007/075277 A1 | 7/2007 |
| WO | WO 2011/158919 A1 | 12/2011 |

OTHER PUBLICATIONS

Extended European Search Report issued Jul. 9, 2015 in Patent Application No. 12860486.5.
Office Action issued Oct. 7, 2015 in Korean Patent Application No. 10-2014-7020008.
U.S. Appl. No. 14/405,943, filed Dec. 5, 2014, Oka, et al.
International Search Report issued Jan. 22, 2013, in PCT/JP2012/083311, filed Dec. 21, 2012.
Combined Taiwanese Office Action and Search Report issued Mar. 25, 2015 in Patent Application No. 101149221 (with English Translation of Category of Documents).

* cited by examiner

VAPOR HEATING IMPLEMENT

TECHNICAL FIELD

The present invention relates to a vapor heating implement.

BACKGROUND OF THE INVENTION

Conventionally, developments of various types of heating implements, which produce heat by oxidation reaction of an oxidizable metal, have been made. In particular, moist heat is useful in more effectively transferring heat to the human body, as compared with dry heat of a hand warmer, and therefore developments of vapor heating implements that can generate vapor continue. Patent Document 1 discloses a vapor heating implement, which comprises a unit for generating vapor heat and a water-retention sheet that is disposed to be adjacent to the unit for generating vapor heat.

RELATED DOCUMENTS

Patent Documents

[Patent Document 1]
Japanese Laid-Open Patent Publication No. 2009-39370

SUMMARY OF INVENTION

According to one aspect of the present invention, there is provided a vapor heating implement, including:

(i) a heating unit having an exothermic layer having an exothermic composition and a water-retention sheet, wherein the exothermic layer and the water-retention sheet are in layers,
wherein the exothermic composition containing an oxidizable metal, water and a water-retention agent,
wherein the water-retention sheet containing a polymer; and
(ii) a bag wherein the bag is at least partially air permeable and is capable of containing the heating unit,
wherein
(A) the content of water in the vapor heating implement is equal to or higher than 40 parts by mass and is equal to or lower than 80 parts by mass for 100 parts by mass of the oxidizable metal;
(B) the content of the water-retention agent in the exothermic composition is equal to or higher than 0.3 parts by mass and is equal to or lower than 20 parts by mass for 100 parts by mass of the oxidizable metal;
(C) the content of water in the exothermic layer is equal to or higher than 8 parts by mass and is equal to or lower than 45 parts by mass for 100 parts by mass of the oxidizable metal; and
(D) the content of water in the water-retention sheet is from 15 to 30 mass % of the maximum water absorption of the water-retention sheet.

BRIEF DESCRIPTION OF THE DRAWINGS

The features and the advantages of the present invention will be more apparent from the following description of certain preferred embodiments taken in conjunction with the accompanying drawings.

DETAILED DESCRIPTION OF THE INVENTION

Embodiments of the present invention will be described in reference to the annexed figures as follows.

In the heating implement described in Patent Document 1, exchange of water occur between the unit for generating vapor heat and the water-retention sheet to provide the suitable water content in the unit for generating vapor heat (more specifically, the water content in the heating element) and the content are adjusted to be appropriate for heat generation. In such Patent Document 1, there was still room for improvement in the start-up of the vapor generation and the endurance of vapor generation.

To solve the problem, the present inventors proposed a vapor heating implement 100 as described below.

Exemplary implements according to the present invention will be described in detail as follows on the basis of the annexed figures. Here, in all figures, the same numeral refers to a similar constituent element, and the detailed description thereof will not be repeated so as to avoid duplications.

The vapor heating implement 100 of the present embodiment will be described in reference to FIG. 1 to FIG. 4. In the beginning, an overview of the vapor heating implement 100 will be described in reference to FIG. 1.

Figure 1:
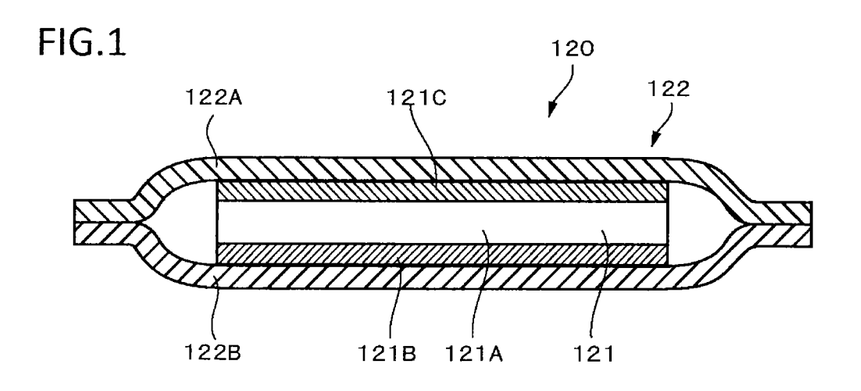
FIG. 1 is a cross-sectional view, illustrating a heating element according to an embodiment of the present invention.

The vapor heating implement 100 is a vapor heating implement that having a heating unit 121 comprising an exothermic layer 121A, which is composed of an exothermic composition containing an oxidizable metal, water and a water-retention agent, and a water-retention sheet 121C layered thereon.

Such vapor heating implement 100 satisfies the following conditions:

(A) the content of water contained in the vapor heating implement 100 is equal to or higher than 40 parts by mass and is equal to or lower than 80 parts by mass for 100 parts by mass of the oxidizable metal;
(B) the content of the water-retention agent contained in the exothermic layer 121A is equal to or higher than 0.3 parts by mass and is equal to or lower than 20 parts by mass for 100 parts by mass of the aforementioned oxidizable metal;
(C) the content of water contained in the exothermic layer 121A is equal to or higher than 8 parts by mass and is equal to or lower than 45 parts by mass for 100 parts by mass of the aforementioned oxidizable metal; and
(D) the content of water contained in the water-retention sheet is from 15 to 30 mass % of the maximum water absorption of the water-retention sheet.

Next, detailed discussions on the vapor heating implement 100 will be made.

The vapor heating implement 100 serves to produce heat through the oxidation reaction of an oxidizable metal to provide a sufficient thermal effect, and is capable of exhibiting a performance of the exothermic temperature as being from 38 to 70 degrees C. in the measurements based upon Japanese Industrial Standard (JIS) S4100. The quantity of water vapor generated from the vapor heating implement 100 is preferably equal to or larger than 0.01 mg/(cm$^2$·min), and is more preferably equal to or larger than 0.03 mg/(cm$^2$·min). Also, the upper limit of the quantity of generated steam is for example, preferably equal to or lower than 0.8 mg/(cm$^2$·min), and more preferably equal to or lower than 0.4 mg/(cm$^2$·min). It is more preferable to be equal to or higher than 0.01 mg/(cm$^2$·min) and equal to or lower than 0.8 mg/(cm$^2$·min), and it is more preferable to be equal to or higher than 0.03 mg/(cm$^2$·min) and equal to or lower than 0.4 mg/(cm$^2$·min). The vapor heating implement 100 has a heating element 120 as shown in FIG. 1.

The heating element 120 having a heating unit 121 and a first bag 122 that is to contain the heating unit 121 therein.

The heating unit 121 having an exothermic layer 121A, a water-retention sheet 121C and a sheet 121B.

The exothermic layer 121A is composed of an exothermic composition containing an oxidizeble metal, water and a water-retention agent.

The oxidizable metal is a metal that is capable of releasing heat by an oxidation reaction, and typically includes, for example, powder or fiber of mixed metals and the like prepared by mixing two or more selected from iron, aluminum, zinc, manganese, magnesium, and calcium. Among these, one or more thereof may be employed. Among these, iron powder is preferable in view of handling-ability, safety, manufacturing cost, storage stability and stability. Typical iron powder includes, for example, reduced iron powder, atomized iron powder and the like.

When the oxidizable metal is powder, the mean particle diameter of the powder is preferably from 10 to 200 μm in terms of the fact that the oxidation reaction is effectively conducted, and the mean particle diameter is more preferably from 20 to 150 μm, and is even more preferably from 20 to 100 μm. Here, the particle diameter of the oxidizable metal means the maximum length in the configuration of the powder, and can be determined by the classification with sieves, dynamic light scattering, laser diffractometry or the like.

In view of the similar aspect, when the oxidizable metal is powder, the mean particle diameter thereof is preferably equal to or larger than 10 μm, and is more preferably equal to or larger than 20 μm. On the other hand, the mean particle diameter is preferably equal to or smaller than 200 μm, and is more preferably equal to or smaller than 150 μm, and even more preferably equal to or smaller than 100 μm.

The content of oxidizable metal in the exothermic composition constituting the exothermic layer 121A is preferably from 100 to 3,000 g/m$^2$ represented with the grammage, and is even more preferably from 200 to 1,500 g/m$^2$. This allows increasing the exothermic temperature of the heating element 120 to a desired temperature. In this case, the content of the iron powder in the heating element 120 can be determined by an ash test pursuant to JIS P8128, or by employing a thermogravimetry device. Another measurement may utilize a property of causing magnetization by applying an external magnetic field to carry out the quantification via the vibrating sample magnetometer test or the like.

In view of the similar aspect, the content of the oxidizable metal in the exothermic composition constituting the exothermic layer 121A is preferably equal to or higher than 100 g/m$^2$ represented by the grammage, and is more preferably equal to or higher than 200 g/m$^2$. On the other hand, the content is preferably equal to or lower than 3,000 g/m$^2$, and is more preferably equal to or lower than 1,500 g/m$^2$.

The water-retention agent is a material having water-retention ability, and typically is, for example, one, two or more selected from carbon components, fiber materials, water-absorbing polymers and water-absorbing powder.

The carbon component possesses a water-retention ability, oxygen supply ability and catalytic ability, and typically, for example, one, two or more selected from activated carbon, acetylene black, and black-lead may be available. Among these, activated carbon is preferably employed, in view of easy adsorption of oxygen in the wetted condition, in view of constant retention of water of the exothermic layer, and in view of easy establishment of the content of the water contained in the water-retention sheet as being from 15 to 30 mass % of the maximum water absorption of the water-retention sheet. More preferably, one, two or more of fine powdered material(s) or granular material(s) selected from coconut shell carbon, wood powder carbon and peat may be employed. Among these, the wood powder carbon is preferable, since the use thereof allows constantly maintaining the moisture level in the exothermic layer to maintain the content of the water contained in the water-retention sheet as being from 15 to 30 mass % of the maximum water absorption of the water-retention sheet.

It is preferable to employ the carbon component having the mean particle diameter of from 10 to 200 μm, not only from the standpoint of achieving the uniform mixing with the oxidizable metal but also from the standpoint of maintaining the content of the water contained in the water-retention sheet as being from 15 to 30 mass % of the maximum water absorption of the water-retention sheet, and it is more preferable to employ that having the mean particle diameter of from 12 to 100 μm. Here, the particle diameter of the carbon component means the maximum length in the configuration of the powder, and can be determined by dynamic light scattering, laser diffractometry or the like. While the carbon component having the form of a powder is preferably employed, those having a form other than powder may alternatively be employed, and for example, those having a fibrous form may be employed.

In view of the similar aspect, the mean particle diameter of the carbon component is equal to or larger than 10 μm, and is preferably equal to or larger than 12 μm. On the other hand, the mean particle diameter of the carbon component is equal to or smaller than 200 μm, and is preferably equal to or smaller than 100 μm.

Preferable fiber materials may include hydrophilic fibers, and among these, cellulose fibers may be more preferably employed. Typical cellulose fibers available here may include chemical fibers (synthetic fibers) and natural fibers.

Typical water-absorbing polymers may include a hydrophilic polymer having a cross-link structure that is capable of absorbing and maintaining a significant amount of liquid, which is 20 times of their own weight.

Typical water-absorbing powders may include one, two or more selected from vermiculite, sawdust, silica gel and pulp powder.

The content of the water-retention agent is from 0.3 to 20 parts by mass over 100 parts by mass of the oxidizable metal, and is more preferably from 1 to 15 parts by mass, and is even more preferably from 3 to 13 parts by mass. This allows accumulating an amount of water required for sustaining the oxidation reaction in the obtained heating element. Another advantage is that a sufficient level of the oxygen supply to the heating element can be achieved to obtain a heating element exhibiting enhanced exothermic efficiency. In addition, the heat capacity of the heating element can be reduced as compared with the acquired amount of the heat generation, so that the temperature elevation due to the heat generation is increased to achieve the desired temperature elevation. In the meantime, the content of the water-retention agent represented by the grammage is preferably from 4 to 290 g/m$^2$, and is more preferably from 7 to 160 g/m$^2$. Having such configuration, the thickness of the exothermic layer 121A can be reduced to provide flexible product without bulkiness. For example, the thickness of the exothermic layer 121A may be equal to or larger than 0.1 mm and equal to or smaller than 1 mm.

In addition to the above, the content of the water-retention agent is preferably equal to or higher than 1 part by mass for 100 parts by mass of the oxidizable metal, and is more preferably equal to or higher than 3 parts by mass. On the other hand, the content of the water-retention agent is preferably equal to or lower than 15 parts by mass for 100 parts by mass of the oxidizable metal, and is more preferably equal to or lower than 13 parts by mass.

In addition, the content of the water-retention agent represented by the grammage is preferably equal to or higher than 4 g/m$^2$ and is more preferably equal to or higher than 7 g/m$^2$. On the other hand, the content of the water-retention agent represented by the grammage is preferably equal to or lower than 290 g/m$^2$, and is, even more preferably equal to or lower than 160 g/m$^2$.

It is preferable in terms of suitably controlling the water content in the exothermic layer that the content of the carbon component in the water-retention agent is equal to or higher than 90 mass % for the whole mass of the water-retention agent, and more preferably equal to or higher than 95 mass %, and even more preferably from 98 mass % to 100 mass %, and it is even more preferable that the water-retention agent is composed only of the carbon component.

Further, the content of the water-absorbing polymer and/or the cellulose fiber in the water-retention agent is equal to or lower than 10 mass % for the whole quantity of the water-retention agent, is preferably equal to or lower than 5 mass % and is more preferably equal to or lower than 2 mass %, and it is even more preferable to contain none of the water-absorbing polymer and/or cellulose fiber in the exothermic layer 121A, since this constitution allows suppressing excessive absorption of water in the exothermic layer 121A to reduce the heat capacity of the heating element in relation to the acquired amount of the heat generation, thereby providing increased temperature elevation by the heat generation, thus providing the desired temperature elevation.

Further, the total content of the water-absorbing polymer and the cellulose fiber in the water-retention agent is preferably equal to or lower than 10 mass % for the whole quantity of the water-retention agent, and more preferably equal to or lower than 5 mass %. The total content of the water-absorbing polymer and the cellulose fiber in the water-retention agent is preferably equal to or lower than 2 mass % for the whole quantity of the water-retention agent. Further, it is preferable to contain neither water-absorbing polymer nor cellulose fiber in the exothermic layer 121A.

The exothermic layer 121A contains water. Water may be one derived from an electrolytic aqueous solution (for example, an aqueous solution of alkali metal, an alkaline earth metal or the like), or alternatively water alone may be added in the exothermic layer 121A, and thus it is not particularly limited.

The water content in the exothermic layer 121A is equal to or larger than 8 parts by mass and equal to or smaller than 45 parts by mass for 100 parts by mass of the oxidizable metal. The water content of the exothermic layer 121A of equal to or smaller than 45 parts by mass for 100 parts by mass of the oxidizable metal allows the exothermic layer 121A sufficiently producing heat to rapidly raise the exothermic temperature (providing shorter temperature-elevation time). On the other hand, the water content of the exothermic layer 121A of equal to or larger than 8 parts by mass for 100 parts by mass of the oxidizable metal ensures the quantity of water required for the exothermic reaction of the exothermic layer 121A to sufficiently sustain the exothermic reaction of the exothermic layer 121A.

As described above, the water content of the exothermic layer 121A is selected so as to fall within the range of equal to or larger than 8 parts by mass and equal to or smaller than 45 parts by mass for 100 parts by mass of the oxidizable metal to provide the exothermic layer 121A exhibiting improved exothermic conditions. More specifically, the water content of the exothermic layer 121A influences the heat generation rate. The water content is selected so as to fall within the range of equal to or larger than 8 parts by mass and equal to or smaller than 45 parts by mass for 100 parts by mass of the oxidizable metal which allows exhibiting sufficient production of heat, rapid rising of the exothermic temperature and sustainment of the constant exothermic temperature.

As described above, since the water content in the exothermic layer 121A is reduced as possible at the initial stage (within about 5 minutes) of the heat generation, for the purpose of attaining the highly exothermic condition of the exothermic layer in a shorter time in order to increase the quantity of water vapor generated at the initial stage (within about 5 minutes) of the heat generation in the present embodiment, enhanced elevation of the exothermic temperature can be achieved. The water content of the exothermic layer 121A is more preferably equal to or larger than 15 parts by mass and equal to or smaller than 40 parts by mass for 100 parts by mass of the oxidizable metal.

The exothermic layer 121A may contain a reaction accelerator agent, in addition to the respective components as described above.

The reaction accelerator agent is employed for the purpose of sustaining the oxidation reaction of the oxidizable metal. In addition, the use of the reaction accelerator agent can break an oxide film on the oxidizable metal to accelerate the oxidation reaction. Typical reaction accelerator agents include, for example, one, two or more selected from sulfates and chlorides of alkali metals and alkaline earth metals. Among these, in view of providing enhanced electroconductivity, chemical stability and production cost, it is preferable to employ one, two or more selected from various types of chlorides such as sodium chloride, potassium chloride, calcium chloride, magnesium chloride, ferrous chloride, ferric chloride and the like; and sodium sulfate.

The content of the reaction accelerator agent is preferably from 2 to 15 parts by mass for 100 parts by mass of the oxidizable metal, in view of sustaining a sufficient amount of heat generation for a longer time duration, and is preferably from 3 to 12 parts by mass.

In view of the similar aspect, the content of the reaction accelerator agent is preferably equal to or larger than 2 parts by mass for 100 parts by mass of the oxidizable metal, and is more preferably equal to or larger than 3 parts by mass, and on the other hand, is preferably equal to or smaller than 15 parts by mass and is more preferably equal to or smaller than 12 parts by mass.

Further, the exothermic layer 121A may contain a thickening agent, in addition to the respective components as described above.

Substances, which are capable of absorbing water to increase consistency or capable of providing a thixotropic property, may be mainly employed for the thickening agent, and a single substance selected from, or a mixture of two or more selected from the following may also be employed: alginates such as sodium alginate and the like; polysaccharide-based thickening agents such as arabian gum, tragacanth gum, locust bean gum, guar gum, arabia gum, carrageenan, agar, xanthan gum and the like; starch-based thickening agents such as dextrin, pregelatinized starch, starch for processing and the like; cellulose derivative-based thickening agents such as carboxymethyl cellulose, ethyl acetate cellulose, hydroxyethyl cellulose, hydroxymethyl cellulose, hydroxypropyl cellulose and the like; thickening agents such as polyvinyl alcohol (PVA) and the like; metallic soap-based thickening agents such as stearate and the like; mineral-based thickening agents such as bentonite and the like.

The content of the thickening agent is preferably from 0.05 to 5 parts by mass for 100 parts by mass of the oxidizable metal, and more preferably from 0.1 to 3 parts by mass. The content of equal to or larger than 0.05 parts by mass is adopted to provide increased viscosity and enhanced stability of the composition of exothermic powder dispersed in water. The content of equal to or smaller than 5 parts by mass is adopted to prevent from being a reason for deterioration in the heat generation characteristics (decreased maximum temperature). The content of from 0.05 to 5 parts by mass allows maintaining the content of water contained in the water-retention sheet as being from 15 to 30 mass % of the maximum water absorption of the water-retention sheet, in addition to allowing the solid contents such as the oxidizable metal, the carbon component and the like being stably dispersed. In addition, this can also provide the thixotropic property to achieve further improved coating performance. Among these, in view of providing enhanced coating performance and maintaining the content of water contained in the water-retention sheet as being from 15 to 30 mass % of the maximum water absorption of the water-retention sheet, the polysaccharide-based thickening agent is preferable, and further, the polysaccharide-based thickening agent having a molecular weight of equal to or higher than 1,000,000 and equal to or lower than 50,000,000 is preferable, and especially, the polysaccharide-based thickening agent having the molecular weight of equal to or higher than 2,000,000 and equal to or lower than 40,000,000 is preferable, and in addition, in view of providing improved coating performance and salt resistance, xanthan gum is preferable.

The content of the thickening agent is preferably equal to or larger than 0.05 parts by mass and is more preferably equal to or larger than 0.1 parts by mass for 100 parts by mass of the oxidizable metal. On the other hand, the content of the thickening agent is preferably equal to or smaller than 5 parts by mass and is further preferably equal to or smaller than 3 parts by mass for 100 parts by mass of the oxidizable metal.

Further, the polysaccharide-based thickening agent preferably has a molecular weight of equal to or higher than 1,000,000, and is more preferably equal to or higher than 2,000,000. On the other hand, the polysaccharide-based thickening agent preferably has a molecular weight of equal to or lower than 50,000,000, and is more preferably equal to or lower than 40,000,000.

It is preferable to contain the polysaccharide-based thickening agent having a molecular weight of from equal to or higher than 1,000,000 and is equal to or lower than 50,000,000 at the content of equal to or larger than 0.05 parts by mass and equal to or smaller than 5 parts by mass for 100 parts by mass of the oxidizable metal.

The water-retention sheet 121C is disposed so as to be directly in contact with the exothermic layer 121A. The water-retention sheet 121C contains water. The content of water is equal to or larger than 15 mass % and equal to or smaller than 30 mass % of the maximum water absorption of the water-retention sheet 121C.

The content of water is selected to be equal to or larger than 15 mass % of the maximum water absorption of the water-retention sheet 121C under the condition of the constitutional matters (A) and (C) to achieve an effect for increasing the quantity of vapor generated in shorter time.

On the other hand, the content of water is selected to be equal to or smaller than 30 mass % of the maximum water absorption of the water-retention sheet 121C to ensure certain level of air permeability of the water-retention sheet 121C and also ensure easy emission of vapor from the water-retention sheet 121C. Since the emission of vapor from the water-retention sheet 121C can be achieved, water in the exothermic layer 121A can be primarily utilized for the heat generation and water in the water-retention sheet 121C can be utilized for vapor. This allows the vapor heating implement 100 releasing desired quantity of vapor and maintaining the condition of enhanced heat generation from the exothermic layer 121A.

In view of increasing the quantity of vapor generated in a shorter time, the content of water is even more preferably equal to or larger than 20 mass % and equal to or smaller than 25 mass % of the maximum water absorption of the water-retention sheet 121C.

In addition to this, the content of water is selected to be equal to or smaller than 30 mass % of the maximum water absorption of the water-retention sheet 121C under the condition of the constitutional matters (A) and (C) to suppress the decrease in the rate of the temperature elevation due to the excessive increase in the heat capacity of the water-retention sheet 121C.

Here, the maximum water absorption of the water-retention sheet 121C can be calculated by the following procedures.

The water-retention sheet 121C was cut into a dimension of 25 cm$^2$ to measure the mass ($W_0$) of the cut piece, and then, the cut piece was dipped in 5 mass % sodium chloride aqueous solution for 5 minutes. The piece was then taken out with tweezers, and was maintained as being hung in the air for one minute during which water that could not be retained in the piece drips, and then the mass ($W_1$) of the piece was measured and the maximum water absorption was calculated according to the following formula.

$$W_{max} = W_1 - W_0.$$

Also, the content of water contained in the water-retention sheet 121C is from 50 to 350 g/m$^2$ represented by the grammage, and is preferably from 180 to 260 g/m$^2$. Since the water content contained in the water-retention sheet serves as a source for the generation of steam, the content of water contained in the water-retention sheet is selected to be equal to or larger than 50 g/m$^2$ represented by the grammage to ensure a certain level of the vapor generation quantity. In addition, since the water-retention sheet acquires a certain level of airflow resistance by absorbing water (i.e., air permeability is reduced than in the dried condition by the swelling due to the water absorption), the water content is selected to be equal to or smaller than 350 g/m$^2$ represented by the grammage to allow easy emission of vapor from the water-retention sheet, and in addition to ensure sufficient air permeability to the exothermic layer, such that sufficient oxygen supply is achieved to obtain the heating element having enhanced heat generation efficiency.

In addition, the content of water contained in the water-retention sheet 121C is preferably equal to or larger than 50 g/m$^2$ represented by the grammage, and is more preferably equal to or larger than 180 g/m$^2$. On the other hand, the content of water contained in the water-retention sheet 121C is preferably equal to or smaller than 350 g/m$^2$ represented by the grammage, and is more preferably equal to or smaller than 260 g/m$^2$.

In addition, air resistance of the water-retention sheet 121C is preferably equal to or lower than 500 seconds/100 ml represented by the air resistance in the condition containing water, and when the air permeability and the vapor permeability are taken into consideration, it is more preferably equal to or lower than for 300 seconds/100 ml, and is even more preferably equal to or lower than 50 seconds/100 ml.

Here, the lower limit of the air resistance in the condition containing water (more specifically, the content of water is equal to or higher than 15 mass % and equal to or lower than 30 mass % of the maximum water absorption of the water-retention sheet 121C) may be, for example, 1 second/100 ml.

The air resistance can be determined by the following procedure.

The air resistance is a value measured according to JIS P 8117 (1998), and is defined as time required for air of 100 ml passing through an area of 6.45 cm$^2$ under constant pressure. Consequently, a larger value of the air resistance means taking longer time for air passage, and thus indicates lower air permeability. Conversely, lower air resistance indicates higher air permeability. As described above, the level of air resistance and the level of air permeability are in an inverse relation. The air resistance can be determined with an Oken type air-permeability and smoothness tester.

Here, a sheet material, which is capable of absorbing and retaining water and has flexibility, are employed for the water-retention sheet 121C. Typical examples of such material include, for example, a paper made of a fiber raw material, or a fiber sheet such as a nonwoven fabric, a woven fabric, a knitted fabric and the like. In addition, a porous member such as a sponge may also be exemplified. Typical fibers as described above includes, for example, fibers having major constituents of natural fibers such as plant fibers, animal fibers and the like and fibers having major constituents of chemical fibers. Typical plant fibers includes, for example, one, two or more selected from cotton, kapok, wood pulp, non-wood pulp, peanut protein fiber, corn protein fiber, soy bean protein fiber, mannan fiber, rubber fiber, hemp, Manila hemp, sisal hemp, New Zealand flax, apocynum venetum, coconut palm, rush grass and straw. Typical animal fibers includes, for example, one, two or more selected from sheep wool, goat wool, mohair wool, cashmere wool, alpaca wool, angola wool, camel wool, vicuna wool, silk, plume, down, feather, algin fiber, chitin fiber and casein fiber. Typical available chemical fibers include, for example, one, two or more selected from rayons, acetates and celluloses.

Among these, a product containing a fiber material composed of the above-described fiber and a water-absorbing polymer is preferable for the water-retention sheet 121C.

Figure 5:
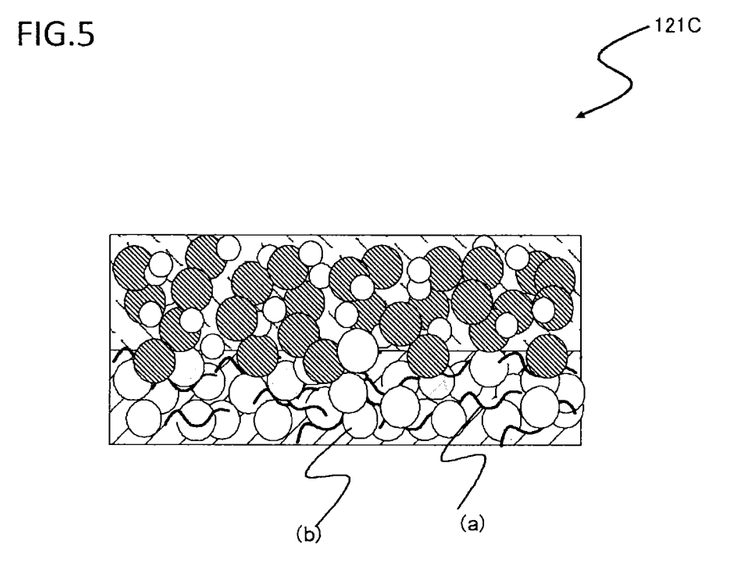
FIG. 5 is a cross-sectional view of the heating unit.

FIG. 5 illustrates the water-retention sheet 121C and the exothermic layer 121A. The component (A) is an oxidizable metal, and the component (B) is a water-retention agent.

FIG. 5 illustrates an example, in which the water-retention sheet 121C includes the component (a): fiber material, and, the component (b): water-absorbing polymer. When the water-retention sheet 121C contains the component (b), the illustrated conformation of the water-retention sheet 121C may include: (i) the component (a) and the component (b) are uniformly mixed to form a single piece of sheet; (ii) the component (b) is disposed between same or different sheets containing the component (a); or (iii) the component (b) is sprayed to form the sheet-like material. Among these, the preferable selection may be the conformation of (ii), since this allows easily control of the water content of the exothermic layer 121A to facilitate the adjustment of the content of water contained in the water-retention sheet 121C as being from 15 to 30 mass % of the maximum water absorption of the water-retention sheet 121C. Meanwhile, the water-retention sheet 121C of the conformation of (ii) may be produced by, for example, a method, in which the component (b): water-absorbing polymer is uniformly sprayed over a sheet containing the component (a), and 200 g/m$^2$ of water is sprayed thereon, and then the same or different type of a sheet containing the component (a) is further layered thereon and compression drying is carried out at 100+/−0.5 degrees C. and a pressure of 5 kg/cm$^2$ until the water content is reduced to equal to or lower than 5 mass %.

The water-absorbing polymer having a cross-link structure, which is capable of absorbing and maintaining a significant amount of liquid that is 20 times of its own weight, is employed as the water-absorbing polymer, such that the content of water contained in the water-retention sheet 121C may be preferably maintained to be from 15 to 30 mass % of the maximum water absorption of the water-retention sheet 121C. A typical shape of the particle of the water-absorbing polymer may be a spherical form, massive form, grape cluster form, fibrous form and the like.

The particle diameter of the water-absorbing polymer is preferably from 1 to 1,000 μm, and is more preferably from 10 to 500 μm. In addition to above, the particle diameter of the water-absorbing polymer particles may be determined by dynamic light scattering, laser diffractometry or the like. The particle diameter of the water-absorbing polymer is preferably equal to or larger than 1 μm, and is more preferably equal to or larger than 10 μm. On the other hand, the particle diameter of the water-absorbing polymer is preferably equal to or smaller than 1,000 μm, and is more preferably equal to or smaller than 500 μm.

Specific examples of the water-absorbing polymer includes one, two or more selected from polyacrylic acids and their salts and polyacrylate graft polymers, such as starch, cross-linked carboxymethyl cellulose, polymers or copolymers of acrylic acids or alkali metal salts of acrylic acids and the like. Among these, polyacrylic acids and their salts and polyacrylate graft polymers such as polymers or copolymers of acrylic acids or alkali metal salts of acrylic acids and the like are preferably employed to sufficiently maintain the content of water contained in the water-retention sheet 121C as being from 15 to 30 mass % of the maximum water absorption of the water-retention sheet 121C.

The ratio of particles of the component (b): water-absorbing polymer to the water-retention sheet 121C is preferably from 10 to 70 mass % under the dried condition, and is more preferably from 20 to 65 mass % to promote the rapid transfer of moisture to the water-retention sheet 121C, thereby suitably maintaining the content of water contained in the water-retention sheet 121C as being from 15 to 30 mass % of the maximum water absorption of the water-retention sheet 121C.

The ratio of particles of the component (b): water-absorbing polymer to the water-retention sheet 121C is preferably equal to or higher than 10 mass % under the dried condition, and is more preferably equal to or higher than 20 mass %. On the other hand, the ratio of particles of the component (b): water-absorbing polymer to the water-retention sheet 121C is preferably equal to or lower than 70 mass % under the dried condition, and is even more preferable equal to or lower than 65 mass %.

The sheet 121B is provided on a surface of the exothermic layer 121A on a side that is opposite to the side of the water-retention sheet 121C. The sheet 121B is in direct contact with the exothermic layer 121A to cover the exothermic layer 121A. A sheet of non-air permeability or poor-air permeability is preferable for the sheet 121B, and for example, a resin sheet is preferably employed. A non-air permeable or poor-air permeable sheet (equal to or higher than 50,000 seconds/100 ml, and preferably equal to or higher than 80,000 seconds/100 ml) is employed, not only to further ensure the emission of vapor from the side of the water-retention sheet 121C, but also to prevent from losing the latent heat of vaporization from the side of the water-retention sheet 121B.

For example, a synthetic resin film may be suitable for the sheet 121B, and typically includes polyethylene films, polyethylene terephthalate films and the like.

Such heating unit 121 as described above is contained in a first bag 122, and the heating unit 121 and the heating element 120 constitutes a bag 122.

The first bag 122 is constituted to include the first sheet 122A and the second sheet 122B, and circumference sections of these sheets 122A and 122B are preferably joined to form a tight seal to constitute the bag 122. Regions except the circumference sections of the sheets 122A and 122B are non-junction regions, and the heating unit 121 is disposed in the non-junction region.

Provided that the first sheet 122A is to be positioned on the side that is closer to the skin of the user (surface on the side of the skin), and the second sheet 122B is to be positioned on the side that is further from the skin of the user, the air resistance of the first sheet 122A is preferably from 1,000 to 7,000 second/100 ml, and is more preferably from 1,500 to 6,000 second/100 ml, and is even more preferably from 1,800 to 5,000 second/100 ml. The air resistance of the first sheet 122A is selected to be equal to or lower than 7,000 second/100 ml to ensure a certain level of the air permeability of the first sheet 122A, so that larger quantity of vapor from the water-retention sheet 121C can be easily discharged toward the outside of the bag 122. The air resistance of the first sheet 122A is selected to be equal to or higher than 1,000 second/100 ml to suitably control the exothermic temperature, thereby avoiding an unusual heat generation.

It is preferable to employ, for example, a porous sheet of a synthetic resin having moisture permeability but having no water permeability for the first sheet 122A having such a air resistance. More specifically, a film manufactured by stretching polyethylene containing calcium carbonate may be employed. When such porous sheet is employed, various types of fiber sheets including one, two or more nonwoven fabric(s) selected from needle punch nonwoven fabric, air through nonwoven fabric and spunbond nonwoven fabric may be laminated over the outer surface of the porous sheet to provide enhanced texture of the first sheet 122A. The first sheet 122A may be an aeration sheet, a portion of or the whole of which has air permeability, or may alternatively be a non-aeration sheet having no air permeability, and may be preferably made of a sheet having higher air permeability than the second sheet 122B (that is, the sheet exhibiting lower air resistance).

In addition to the above, provided that the first sheet 122A is to be positioned on the side that is closer to the skin of the user (surface on the side of the skin), and the second sheet 122B is to be positioned on the side that is further from the skin of the user, the air resistance (JIS P 8117) of the first sheet 122A is preferably equal to or lower than 7,000 seconds/100 ml, is more preferably equal to or lower than 6,000 seconds/100 ml, and even more preferably equal to or lower than 5,000 seconds/100 ml. On the other hand, the air resistance (JIS P 8117) of the first bag sheet 20a is preferably equal to or higher than 1,000 seconds/100 ml, is more preferably equal to or higher than 1,500 seconds/100 ml, and even more preferably equal to or higher than 1,800 seconds/100 ml.

The second sheet 122B may be an aeration sheet, a portion of or the whole of which has air permeability, or may alternatively be a non-aeration sheet having no air permeability, and may be preferably made of a sheet having lower air permeability than the first sheet 122A (that is, the sheet exhibiting higher air resistance).

When the second sheet 122B is composed of a non-aeration sheet, a film manufactured with synthetic resin having a single layer or multiple layers may be employed, or various types of fiber sheets including one, two or more nonwoven fabric(s) selected from needle punch nonwoven fabric, air through nonwoven fabric and spun bond nonwoven fabric may be laminated over the outer surface of the aforementioned film manufactured with synthetic resin having a single layer or multiple layers to provide enhanced texture of the second sheet 122B. More specifically, a dual-layered film composed of a polyethylene film and a polyethylene terephthalate film, a laminate film composed of a polyethylene film and a nonwoven fabric, a laminate film composed of a polyethylene film and a pulp sheet and the like may be employed, and the laminate film composed of a polyethylene film and a pulp sheet is especially preferable.

When the second sheet 122B is an aeration sheet, the bag sheet that is the same as the first sheet 122A may be employed, or a different bag sheet may alternatively be employed. When a different bag sheet is employed, the air resistance of the second sheet 122B is preferably equal to or higher than 50,000 seconds/100 ml, and is more preferably equal to or higher than 80,000 seconds/100 ml, as long as the air permeability of the second sheet 122B is lower than the air permeability of the first sheet 122A. The air permeability of the second sheet 122B is selected to be lower than that of the first sheet 122A, such that vapor generated in the heating unit 121 can be discharged from the side of the first sheet 122A. It is especially preferable that the air resistance of the first sheet 122A is selected to be from 2,000 to 4,000 second/100 ml and the air resistance of the second sheet 122B is selected to be equal to or higher than 100,000 second/100 ml. The above described air resistances allow enhanced oxidation reaction of the oxidizable metal, and in addition allow emission of a larger quantity of water vapor from the side of the first sheet 122A.

Here, the heating unit 121 is arranged so that the side of the water-retention sheet 121C faces the skin surface of the user. More specifically, the heating unit 121 is arranged in the bag 122 so that the side of the water-retention sheet 121C is disposed to be closer to the skin and the side of the sheet 121B is disposed to be further from the skin. In the present embodiment, the water-retention sheet 121C is arranged on the side of the first sheet 122A and the sheet 121B is arranged on the side of the second sheet 122B. This allows efficient emission of vapor generated from the water-retention sheet 121C through the first sheet 122A.

If only the water-retention sheet 121C is formed on the exothermic layer 121A and none of the sheet 121B is employed, there is a risk that the exothermic layer may be in direct contact with the second sheet 122B, and thus, in order to avoid the possibility that the air permeability of the second sheet 122B is changed due to the adhesion of the exothermic layer, it is preferable to compose the second sheet 122B of a non-aeration sheet.

A single heating element 120 may be housed in the bag 122, or those in multiple-layered configuration may alternatively be housed therein.

Subsequently, an example of a method for producing the heating element 120 will be described. The heating element 120 can be produced by applying, for example, a composition of exothermic powder dispersed in water containing an oxidizable metal, a water absorption agent and water, over the water-retention sheet 120C. While the production of the composition of exothermic powder dispersed in water is carried out by mixing all the above-described components at one time, an alternative way may be that the reaction accelerator agent is dissolved in a mixture that has been preliminarily produced by dissolving the thickening agent in water to prepare an aqueous solution, and then, a pre-mixture of the oxidizable metal and the water absorption agent is added therein.

While the mixing of the reaction accelerator agent may be conducted simultaneously with the mixing of other components in the composition of exothermic powder dispersed in water, an alternative way may be that the composition of exothermic powder dispersed in water is applied, and then a solution of the reaction accelerator agent dissolved in water is added thereto via penetration, atomization or drip and the like, or another alternative way may be to spray the powder of the reaction accelerator agent.

When the above-described composition of exothermic powder dispersed in water is applied over at least one surface of the water-retention sheet 121C, at least a portion of water in the composition of exothermic powder dispersed in water is absorbed by the water-retention sheet 121C to form the exothermic layer 121A on the water-retention sheet 121C. The exothermic layer 121A is composed of residual components that have not been absorbed by the water-retention sheet 121C. The exothermic layer 121A may be present on the water-retention sheet 121C, or alternatively, a lower section of the exothermic layer 121A may be leastwise partly buried in the water-retention layer sheet 121C. In addition, the exothermic layer 121A may be provided on one surface of the water-retention sheet 121C, or may be provided to be interposed between the water-retention sheet 121C and the sheet 121B. FIG. 1 illustrates an example of the exothermic layer 121A, which is interposed between the water-retention sheet 121C and the sheet 121B.

Figure 6:
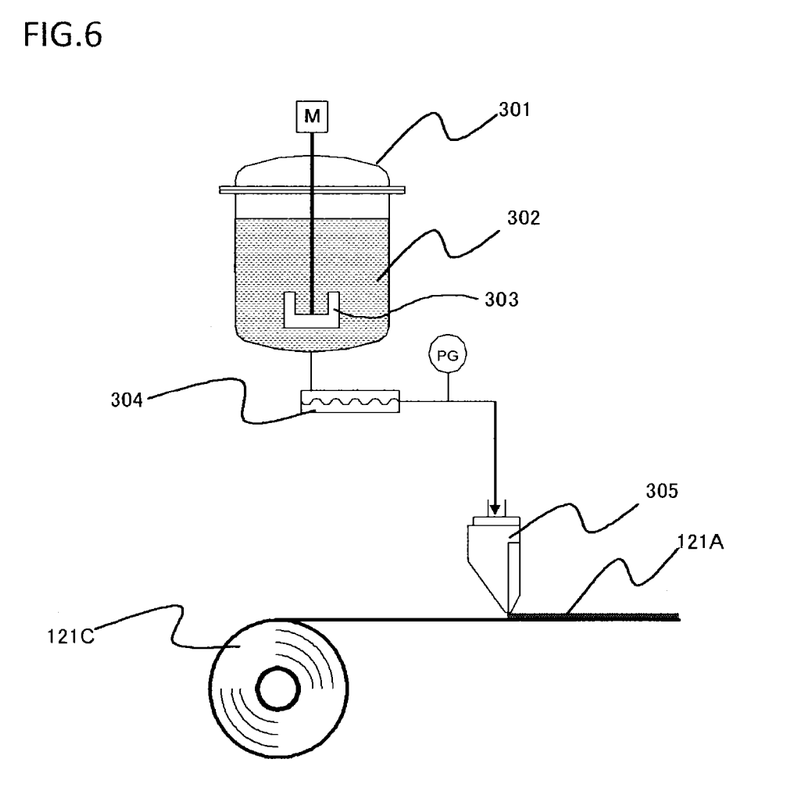
FIG. 6 is a schematic view, illustrating a production apparatus.

FIG. 6 is a diagram, which is helpful for more specifically describing this production method. First of all, a composition of exothermic powder dispersed in water 302 containing raw materials constituting the exothermic layer 121A is prepared in a coating vessel 301. The composition of exothermic powder dispersed in water 302 may be stirred by a stirrer 303 to more uniformity disperse the components that are insoluble in water, which typically includes the oxidizable metals, and the water absorption agents and the like.

Then, the composition of exothermic powder dispersed in water 302 is pumped to a die head 305 by a pump 304. The pumped composition of exothermic powder dispersed in water 302 is pressurized and pushed by employing the die head 305 to be applied over the water-retention sheet 121C. At this time, the coating grammage of the composition of exothermic powder dispersed in water 302 is preferably from 160 to 4,800 g/m$^2$, and is more preferably from 320 to 2,200 g/m$^2$.

While FIG. 6 illustrates the coating process via the die coating, the coating method is not limited thereto, and for example, roll coating, screen printing, roll gravure, knife cording, curtain coater and the like may be applicable.

A continuous elongated workpiece of the exothermic material comprising the exothermic layer 121A and the water-retention sheet 121C is obtained by the above described operations, and the obtained workpiece is cut into pieces having desired sizes, and further the sheet 121B is provided therein and the member is contained in the bag 122 to form the heating element 120.

Figure 2:
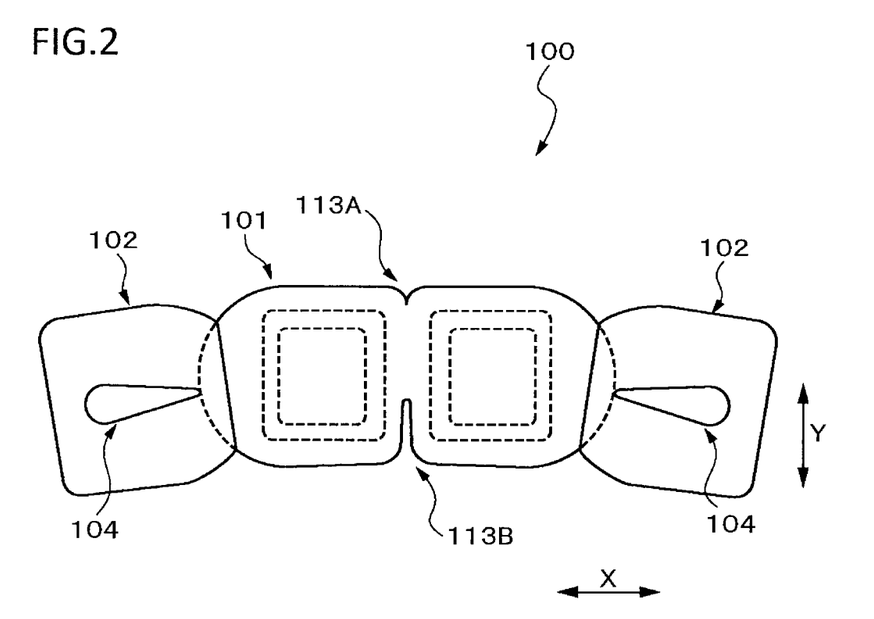
FIG. 2 is a plan view, illustrating the vapor heating implement.

In the next, other constitutions of the vapor heating implement 100 will be described in reference to FIG. 2 to FIG. 4.

The vapor heating implement 100 serves as providing sufficient heating effect with heat generated by the oxidation reaction of the oxidizable metal, and is capable of exhibiting the performance of the exothermic temperature of from 40 to 70 degrees C. in the measurement based upon Japanese Industrial Standard (JIS) S4100. The vapor heating implement 100 is a vapor heat generation implement accompanied with the generation of water vapor.

The vapor heating implement 100 in the present embodiment is a so-called eye mask type implement, and is employed for providing water vapor that is heated to a predetermined temperature (hereinafter, also referred to as "vapor heat") to the eyes and circumferences thereof by being in close contact with the eyes of humans and circumferences thereof.

The vapor heating implement 100 includes a main body 101 and ear hooks 102, each having a hole 104 formed therein, in which the ear is inserted.

The main body 101 has an elongated shape having an elongating direction X and a width direction Y perpendicular to the elongating direction. The main body 101 has substantially an oval shape. The ear hooks 102 are employed as a pair, and each of the ear hooks 102 is mounted to a respective end in the elongating direction of the main body 101 (X direction). The vapor heating implement 100 is put on by hooking the respective ear hooks 102 on the ears of the user so as to cover both eyes of the user with the main body 101. Under such condition of wearing the implement, the vapor heat generated from the vapor heating implement 100 comes in contact with the eyes of the user to reduce eyestrain, hyperemia and asthenopia, and also to achieve a relaxation feel. Further, a hypnagogic feel is also achieved.

Figure 3:
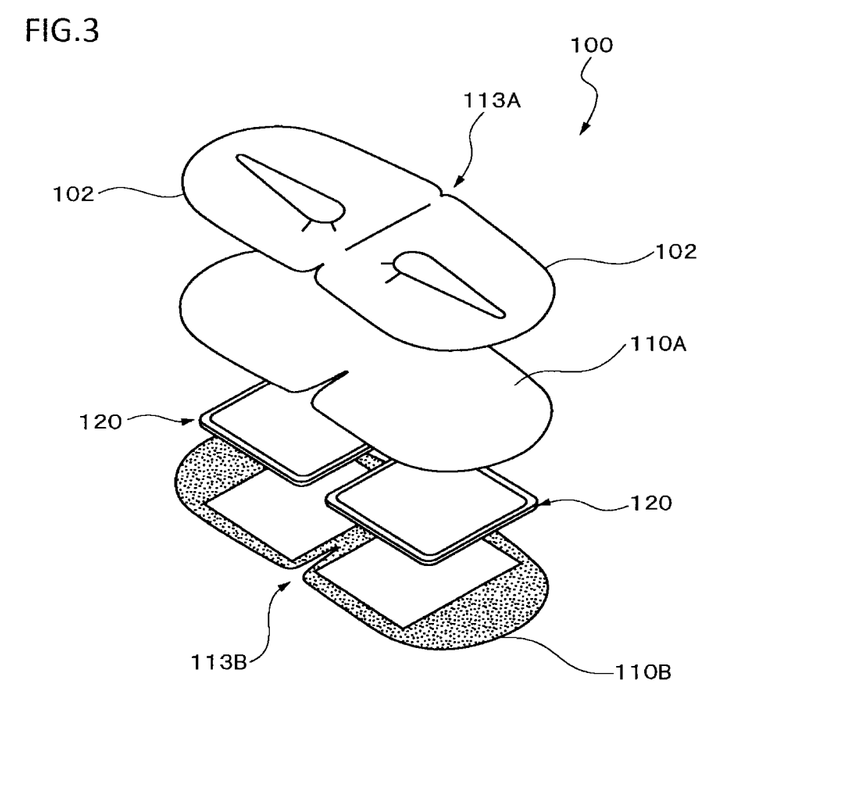
FIG. 3 is an exploded perspective view of the vapor heating implement.

FIG. 3 shows an exploded perspective view of the vapor heating implement 100. In this diagram, the ear hook 102 is disposed on the main body 101. FIG. 4 also shows a cross-sectional view of the vapor heating implement 100 along the X direction. The main body 101 of the vapor heating implement 100 includes the above-described heating element 120 and a second bag 110 for housing the heating element 120 therein.

The second bag 110 includes a second bag-first sheet 110A positioned on the side close to the skin of the user and a second bag-second sheet 110B positioned on the side far from the skin of the user.

The second bag-first sheet 110A has a grammage of from 20 to 200 g/m$^2$, and more preferably has a grammage of from 20 to 120 g/m², in view of preventing from diaphanous appearance and in view of providing certain levels of heat retention, flexibility and thickness.

The second bag-second sheet 110B also has a grammage of from 20 to 200 g/m² in the same reason as the second bag-first sheet 110A, and more preferably has a grammage of from 20 to 120 g/m², in view of preventing from diaphanous appearance and in view of providing certain levels of heat retention, flexibility and thickness.

Here, in view to releasing vapor and supplying oxygen to the exothermic layer, the air resistances of both the second bag-first sheet 110A and the second bag-second sheet 110B are equal to or lower than 6,000 seconds/100 ml and more preferably equal to or lower than 1,000 seconds/100 ml. Water vapor evaporated from the water-retention sheet 121C passes through the first sheet 122A and the first bag sheet 110A to reach the skin.

The second bag-first sheet 110A and the second bag-second sheet 110B have an equivalent shape, and are substantially oval. Then, the outer shapes of the second bag-first sheet 110A and the second bag-second sheet 110B form the outer shape of the main body 101. The second bag-first sheet 110A is deposited over the second bag-second sheet 110B and the circumference sections thereof are joined and those central sections in the X direction are also joined along the Y direction to form a bag 110 having two spaces in the interior thereof. Then, the heating elements 120 are contained in the respective spaces, respectively. In order to join the second bag-first sheet 110A to the second bag-second sheet 110B, a hot melt adhesive agent, for example, may be employed. While the heating element 120 is contained in the bag 110, the heating element 120 is fixed to the bag 110 with an adhesive agent, heat sealing (not shown) or the like.

Fiber sheets including nonwoven fabrics, for example, may be employed for the second bag-first sheet 110A and the second bag-second sheet 110B.

Formed in the bag 110 are substantially V-shaped notched sections 113A and 113B, which are disposed in positions of the central part of the two longer sides extending toward the X direction, and have shapes of being notched inwardly along the Y direction from the longer side. The notched sections 113A and 113B have different notched outlines. When the vapor heating implement 100 is put, the notched section 113A is situated between the eyebrows of the user, or the vicinity thereof. When the vapor heating implement 100 is put, the notched section 113B is situated on the nasal bridge of the user. Consequently, the notched section 113B has a larger notched profile than the notched section 113A. Alternatively, at least one of the notched sections 113A and 113B shown in FIG. 2 may be a slit.

Figure 4:
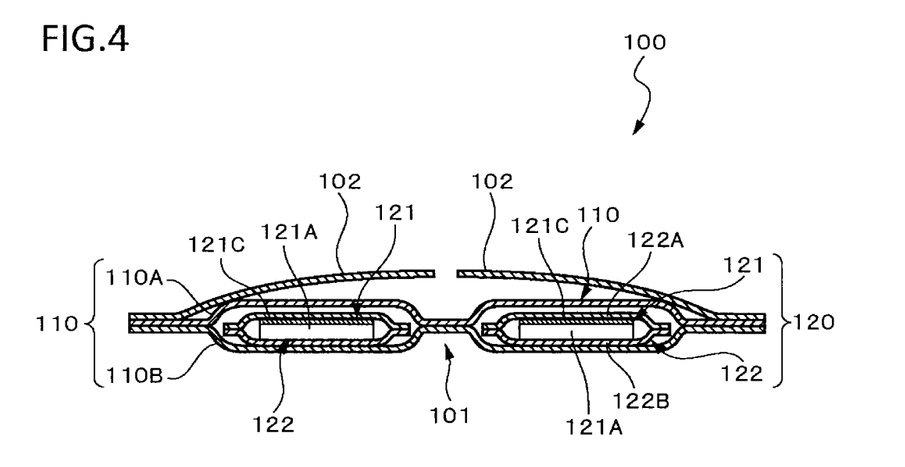
FIG. 4 is a cross-sectional view of the vapor heating implement.

The ear hook 102 in the vapor heating implement 100 is, in the condition before use, disposed on the first bag sheet 110A in the main body 101 as shown in FIG. 3 and FIG. 4. On the use of the vapor heating implement 100, the ear hook 102 is inverted toward the outside along the X direction to attain an opened condition as shown in FIG. 2. In the condition before use, or more specifically in the condition that the right and left ear hooks 102 are positioned on the main body 101, the profile formed by the right and left ear hooks 102 is substantially equivalent to the profile of the main body 101. A material same as that of the bag 110 may be employed for the ear hooks 102.

The vapor heating implement 100 of the present embodiment is wrapped before the use by a package material (not shown), the entire of which has oxygen barrier property, to prevent the heating unit 121 from being in contact with oxygen in the air.

In the heating implement 100 as described above, the content of water contained in the heating implement 100 is equal to or larger than 40 parts by mass and equal to or smaller than 80 parts by mass for 100 parts by mass of the oxidizable metal.

The content of water contained in the whole heating implement 100 is selected to fall within the range of equal to or larger than 40 parts by mass and equal to or smaller than 80 parts by mass for 100 parts by mass of the oxidizable metal, so that the heat capacity of the heating element can be reduced in relation to the acquired amount of the heat generation, thereby providing increased temperature elevation by the heat generation, thus providing the desired temperature elevation, as well as ensuring enhanced exothermic property and also suppressing deterioration in the exothermic temperature. Among these, it is preferable to be equal to or larger than 50 parts by mass and equal to or smaller than 72 parts by mass.

It is apparent that the present invention is not limited to the above described embodiments, and any modifications, changes in the constitutions and the arrangements and improvements without departing from the scope and spirit of the invention are included in the present invention.

While, for example, the vapor heating implement of the type of the eye mask for the use in contact with the eyes of the user has been exemplified in the aforementioned embodiment, it is not intended to be limited thereto.

For example, the vapor heating implement may alternatively be those for the use in contact with the shoulder, knee, and elbow of the user. In such application, it is preferable to provide a fixing means such as a cohesive agent and the like, in place of the ear hooks 102.

Further, while the heating unit 121 includes the sheet 121B in the aforementioned embodiment, the present invention is not limited thereto, and the heating unit 121 may alternatively contain none of the sheet 121B.

Concerning the embodiment as described above, the present invention will further disclose the following compositions and applications thereof.

<1>

A vapor heating implement, comprising:
(i) a heating unit comprising an exothermic layer having an exothermic composition and a water-retention sheet, wherein the exothermic layer and the water-retention sheet are in layers,
wherein said exothermic composition comprises an oxidizable metal, water and a water-retention agent,
wherein said water-retention sheet comprises a polymer; and
(ii) a bag wherein the bag is at least partially air permeable and is capable of containing said heating unit, wherein
(A) the content of water in the vapor heating implement is equal to or higher than 40 parts by mass and is equal to or lower than 80 parts by mass for 100 parts by mass of said oxidizable metal;
(B) the content of said water-retention agent in the exothermic composition is equal to or higher than 0.3 parts by mass and is equal to or lower than 20 parts by mass for 100 parts by mass of said oxidizable metal;
(C) the content of water in said exothermic layer is equal to or higher than 8 parts by mass and is equal to or lower than 45 parts by mass for 100 parts by mass of said oxidizable metal; and
(D) the content of water in said water-retention sheet is from 15 to 30 mass % of the maximum water absorption of the water-retention sheet.

<2>

The vapor heating implement as described in <1>, wherein the aforementioned water-retention agent comprises activated carbon, and the content of the aforementioned activated carbon in the aforementioned water-retention agent is from 90 to 100 mass %.

<3>

The vapor heating implement as described in <1> or <2>, wherein the aforementioned heating unit is arranged so that a side of the aforementioned water-retention sheet faces a skin surface of a user.

<4>

The vapor heating implement as described in any one of <1> to <3>, wherein a sheet having an air resistance of equal to or higher than 50,000 seconds/100 ml is adhered on the aforementioned exothermic layer on a side that is opposite to the side of the water-retention sheet.

<5>

The vapor heating implement as described in any one of <1> to <4>, wherein (E) air resistance of the aforementioned water-retention sheet is equal to or lower than 500 seconds/100 ml.

<6>

The vapor heating implement as described in any one of <1> to <5>, wherein the aforementioned heating unit is contained within the bag, and air resistance of at least one surface of the aforementioned bag is from 1,000 to 7,000 seconds/100 ml.

<7>

The vapor heating implement as described in any one of <1> to <6>, wherein the aforementioned heating unit is contained within the bag, and air resistance of the sheet positioned on a side further from a skin of a user for the aforementioned bag is equal to or higher than 50,000 seconds/100 ml.

<8>

The vapor heating implement as described in any one of <1> to <7>, wherein the content of water in the aforementioned water-retention sheet, represented by grammage, is from 50 to 350 g/m$^2$.

<9>

The vapor heating implement as described in any one of <1> to <8>, wherein the aforementioned water-retention sheet comprises a fiber-based material and a water-absorbing polymer.

<10>

The vapor heating implement as described in any one of <1> to <9>, wherein the aforementioned exothermic layer further comprises a polysaccharide-based thickening agent having a molecular weight of equal to or higher than 1,000,000 and equal to or lower than 50,000,000.

<11>

The vapor heating implement as described in any one of <1> to <10>, wherein the content of the polysaccharide-based thickening agent having a molecular weight of equal to or higher than 1,000,000 and equal to or lower than 50,000,000 is from 0.05 to 5 parts by mass for 100 parts by mass of the oxidizable metal.

<12>

The vapor heating implement as described in any one of <1> to <11>, wherein the mean particle diameter of the oxidizable metal is from 10 to 200 µm.

<13>

The vapor heating implement as described in any one of <1> to <12>, wherein the content of the oxidizable metal is from 100 to 3,000 g/m$^2$.

<14>

The vapor heating implement as described in any one of <1> to <13>, wherein the content of the water-retention agent is from 3 to 13 parts by mass for 100 parts by mass of the oxidizable metal.

<15>

The vapor heating implement as described in any one of <1> to <14>, wherein the mean particle diameter of the carbon component is from 10 to 200 µm.

<16>

The vapor heating implement as described in any one of <1> to <15>, wherein the content of the water-retention agent is from 4 to 290 g/m$^2$.

<17>

The vapor heating implement as described in any one of <1> to <16>, wherein the content of the carbon component is equal to or larger than 98 mass % for the mass of the water-retention agent.

<18>

The vapor heating implement as described in any one of <1> to <17>, wherein the content(s) of the water-absorbing polymer and/or the cellulose fiber in the water-retention agent is equal to or smaller than 10 mass %.

<19>

The vapor heating implement as described in any one of <1> to <18>, wherein the content of water contained in the exothermic layer is equal to or larger than 15 parts by mass and equal to or smaller than 40 parts by mass for 100 parts by mass of the oxidizable metal.

<20>

The vapor heating implement as described in any one of <1> to <19>, wherein the exothermic layer further comprises a reaction accelerator agent, and content of the reaction accelerator agent is from 2 to 15 parts by mass for 100 parts by mass of the oxidizable metal.

<21>

The vapor heating implement as described in any one of <1> to <20>, wherein the content of water contained in the water-retention sheet is from 20 to 25 mass % of the maximum water absorption of the water-retention sheet.

<22>

The vapor heating implement as described in any one of <1> to <21>, wherein the content of water contained in the water-retention sheet is from 180 to 260 g/m$^2$.

<23>

The vapor heating implement as described in any one of <1> to <22>, wherein the air resistance of the water-retention sheet is equal to or lower than for 50 seconds/100 ml under the condition of containing water.

<24>

The vapor heating implement as described in any one of <1> to <23>, wherein the water-retention sheet comprises a water-absorbing polymer, and particle diameter of the water-absorbing polymer is from 1 to 1,000 µm.

<25>

The vapor heating implement as described in any one of <1> to <24>, wherein the ratio of the water-absorbing polymer in the water-retention sheet is from 10 to 70 mass % under the dried condition.

<26>

The vapor heating implement as described in any one of <1> to <25>, wherein a sheet having air resistance of equal to or higher than 80,000 second/100 ml is adhered on a side that is opposite to the side of the water-retention sheet.

<27>

The vapor heating implement as described in any one of <1> to <26>, wherein said heating unit is contained in a bag, and air resistance of the sheet positioned on a side of the bag far from a skin of a user is equal to or higher than 80,000 second/100 ml.

<28>

The vapor heating implement as described in any one of <1> to <27>, wherein said heating unit is contained in a bag, and the bag is further contained in a second bag having air permeability.

<29>

The vapor heating implement as described in any one of <1> to <28>, comprises a main body and an ear hook.

<30>

The vapor heating implement as described in any one of <1> to <29>, wherein the content of water contained in the vapor heating implement is equal to or larger than 50 parts by mass and equal to or smaller than 72 parts by mass for 100 parts by mass of the oxidizable metal.

EXAMPLES

Next, Examples will be described.

Examples 1 to 4

Vapor heating implements, each having a structure as shown in FIG. 1, were produced as follows.

[Preparation of Composition of Exothermic Powder Dispersed in Water]

An oxidizable metal, a water-retention agent, water, a reaction accelerator agent and a thickening agent were prepared according to the relative proportions of the components as shown in Table 1, and the productions were carried out by the following procedures. The thickening agent was dissolved in water, and then the reaction accelerator agent was dissolved therein to prepare an aqueous solution. Meanwhile, a powder mixture made by pre-mixing an oxidizable metal and a water-retention agent was prepared, and such pre-mixed powder was added to the aqueous solution, and then the mixture was stirred with disc turbine stirring blades at 150 rpm for 10 minutes to obtain a composition of exothermic powder dispersed in water in a form of slurry.

Here, information on product types, product names and/or manufacturers for the oxidizable metal, the water-retention agent, water, the reaction accelerator agent, and the thickening agent are as follows. These are also the same as in Comparative Example 1 to be discussed later.

oxidizable metal: iron powder: (iron powder RKH, mean particle diameter 45 μm, commercially available from DOWA IP CREATION Co., Ltd.);

water-retention agent: activated carbon (CARBORAFFIN, mean particle diameter 40 μm, commercially available from Japan EnviroChemicals, Ltd.);

water: tap water reaction accelerator agent: sodium chloride (Japanese Pharmacopoeia sodium chloride, commercially available from Otsuka Chemical Co., Ltd.); and thickening agent: Xanthan gum, (molecular weight 2,000,000, Echogum BT commercially available from DSP GOKYO FOOD & CHEMICAL Co., Ltd.),

[Production of Heating Unit 121]

A polymer sheet was manufactured by layering:
a paper made of wood pulp (20 g/m², commercially available from Inokami Co., Ltd.); a water-absorbing polymer (sodium polyacrylate, spherical, mean particle diameter 300 μm, 30 g/m² 50 g/m², AQUALIC CA, commercially available from Nippon Shokubai Co., Ltd.); and another paper made of wood pulp (30 g/m², commercially available from Inokami Co., Ltd.) and combining them into a single sheet to be employed as the water-retention sheet 121C.

The above-described composition of exothermic powder dispersed in water was applied on the water-retention sheet 121C of 25 cm² (5 cm×5 cm) over the area of 25 cm² (5 cm×5 cm) (see Table 1 for coating quantity). Thereafter, the product was covered with the sheet 121B. The sheet 121B was a sheet having non-air permeability (equal to or larger than 50,000 seconds/100 ml) and was a polyethylene film.

Comparative Example 1

A composition of exothermic powder dispersed in water was prepared according to the relative proportions of the components shown in Table 1 in the same procedure as in Example 1, and the above-described composition of exothermic powder dispersed in water was applied on the water-retention sheet 121C of 25 cm² (5 cm×5 cm) over the area of 25 cm² (5 cm×5 cm) (see Table 1 for coating quantity). Then, before being covered with the sheet 121B, 5% salt water was further added to eventually manufacture an exothermic layer containing 63.8 parts by mass of water for 100 parts by mass of iron powder.

[Production of Vapor Heating Implement]

Each of the heating elements of Examples 1 to 4 and Comparative Example 1 was put in the bag having air permeability (first bag sheet having air resistance of 2,500 seconds/100 ml on the skin side, and first bag sheet having non-air permeability on the side opposite to the skin side, 6.5 cm×6.5 cm), and then the circumference section thereof was tightly sealed. At this time, the heating unit was arranged so that the side of the water-retention sheet could be positioned on the side of the first bag sheet in Examples 1 to 4 and Comparative Example 1.

Further, the heating unit contained in the bag (heating element) was put in an exterior bag (second bag, 7.5 cm×7.5 cm) made of an air through nonwoven fabric (skin side, air resistance 1 second/100 ml, grammage 30 g/m²) and a needle punch nonwoven fabric (side opposite to skin, air resistance 1 second/100 ml, grammage 80 g/m²), and the circumference section thereof was tightly sealed to obtain a vapor heating implement. The vapor heating implement was stored in an oxygen insulation bag until an evaluation, as will be discussed later, was started. Further, a series of operations were conducted under a nitrogen gas-stream atmosphere.

[Evaluations]

The following evaluations were made on the heating elements of Examples 1 to 4 and Comparative Example 1, and the vapor heating implement containing thereof. The evaluation results were shown in Table 1.

1. Measurements of Water Content

<<1>> Water Percentage ($R_{H2O}$) and Water Content ($W_{121}$) of Exothermic Layer 2 g of the exothermic layer, which had been formed on the water-retention sheet, was collected, and a moisture tester (Kett moisture tester, FD-240, commercially available from Kett Electric Laboratory Co., Ltd.) was employed to determine the water percentage $R_{H2O}$ of the exothermic layer by measuring the quantity of the exhausted water during thermal drying at 120 degrees C. for 15 minutes.

water percentage of exothermic layer ($R_{H2O}$)=content of emitted water/sample quantity (2 g)   (formula 1)

water content in exothermic layer ($W_{121}$)=coating quantity×solid content percentage in exothermic composition (total of relative proportions of components except water/total of relative proportions of components)×measured water percentage $R_{H2O}$/(1−measured water percentage $R_{H2O}$)   (formula 2).

<<2>> Water Content of Water-Retention Sheet ($W_{121C}$)

As represented by the following formula (formula 3), the water content of the water-retention sheet was calculated with the following formula.

water content of water-retention sheet ($W_{121C}$)=coating quantity×water percentage in exothermic composition (relative proportion of water/total of relative proportions of components)−(<<1>> (water content of exothermic layer $W_{121}$)    (formula 3).

<<3>> Maximum Water Absorption of Water-Retention Sheet ($W_{max}$)

Water-retention sheet 121C [paper made of wood pulp (20 g/m$^2$), water-absorbing polymer (50 g/m$^2$) and paper made of wood pulp (30 g/m$^2$), Production method: The water-absorbing polymer was uniformly sprayed over the upper surface of the paper made of wood pulp (20 g/m$^2$), and water was over-sprayed at 200 g/m$^2$, and then the paper made of wood pulp (30 g/m$^2$) was laminated thereon and was press-dried at 100 degrees C. (+/−5 degrees C.); thickness 0.5 mm. water content in dried condition: equal to or lower than 5%] before being coated with exothermic composition was cut into a dimension of 25 cm$^2$ to measure the mass ($W_0$) of the cut piece, and then, the cut piece was dipped in 5 mass % sodium chloride aqueous solution for five minutes. The piece was then taken out with tweezers, and was maintained as being hung for one minute so as to drip an amount of water that could not be retained by the piece, and then the mass of the piece was measured and the maximum water absorption was calculated according to the following formula.

$$W_{max}=W_1-W_0$$

<<4>> Air Resistance of Water-Retention Sheet

The vapor heating implement was taken out from the oxygen insulation bag, and the exothermic layer 121A on the water-retention sheet 121C was eliminated to be removed.

Thereafter, the measurements were carried out according to JIS P8117 (1998) by employing an Oken type air-permeability and smoothness tester.

2. Measurement of Heat Generation (Maximum Temperature, Temperature Elevation Time)

A measurement device based upon JIS S 4100 was employed and an outer bag of the vapor heating implement 100 was arranged so that a surface thereof on a side of the skin was oriented outward, and a temperature sensor was fixedly installed on another surface opposing the side of the skin. The temperature sensor was fixed on the measurement surface with a meshed material (made of polyester, double raschel dough of 8 mm thick). After opening the bag, the temperature was measured at 10 second-intervals for 40 minutes, and the maximum temperature was measured. More specifically, evaluations were carried out for the rising of the temperature (time required for the exothermic temperature reaching 45 degrees from starting at 35 degrees C.) and the maximum temperature (degree C.) after opening the oxygen insulation bag.

(Quantity of Generated Vapor)

Figure 7:
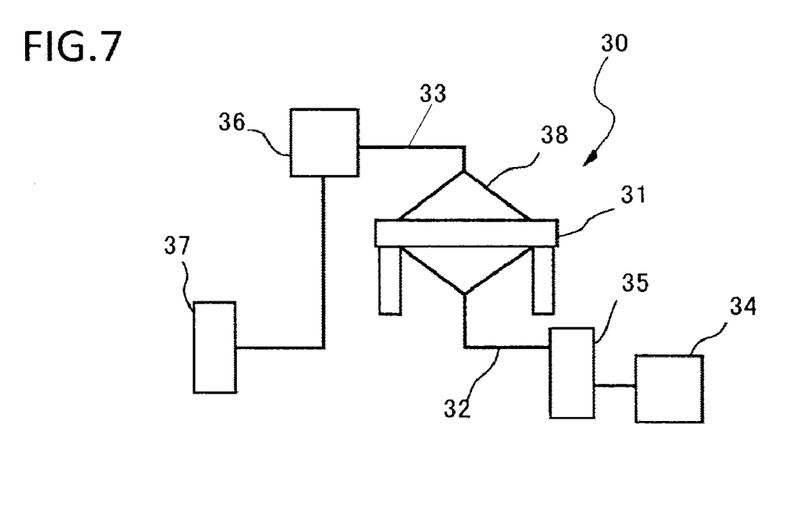
FIG. 7 is a schematic view, illustrating a device for measuring a quantity of generated steam.

The measurements were carried out as follows by employing a device 30 shown in FIG. 7. The device 30 shown in FIG. 7 comprises a measurement chamber (capacity: 2.1 L) 31 made of aluminum, an inflow passageway 32 for introducing dehumidified air (humidity: lower than 2%, flow rate: 2.1 L/min.) in the lower section of the measurement chamber 31, and an outflow passageway 33 for discharging air from the upper portion of the measurement chamber 31. The inflow passageway 32 was provided with an inlet thermo-hygrometer 34 and an inlet flow meter 35 mounted thereto. On the other hand, the outflow passageway 33 was provided with an outlet thermo-hygrometer 36 and an outlet flow meter 37 mounted thereto. A thermometer (thermistor) 38 was mounted in the measurement chamber 31. A device exhibiting temperature resolution of about 0.01 degrees C. was employed for the thermometer 38. The vapor heating implement was taken out from the oxygen insulation bag at a measurement environmental temperature of 30 degrees C. (30+/−1 degree C.), and was placed in the measurement chamber 31 so that the water vapor emission surface (surface on the side of the first bag sheet) was upwardly oriented. The thermometer 38 with a metallic ball (4.5 g) was placed thereon. Under this condition, dehumidified air was flowed from the lower section of the measurement chamber 31. Differences in the absolute humidity between before and after the air was entered in the measurement chamber 31 were obtained from the temperature and the humidity measured by the inlet thermo-hygrometer 34 and the outlet thermo-hygrometer 36. Further, the quantity of water vapor released by the vapor heating implement discharged was calculated on the basis of the flow rates measured with the inlet flow meter 35 and the outlet flow meter 37. The details of this device are described in a Japanese Laid-Open Patent Publication No. 2004-73688, which is a former patent application of the applicant of the present application.

The vapor quantity in 10 minutes from opening the bag and the vapor quantity in 20 minutes from opening the bag were measured by employing the device 30.

The maximum temperature was high and the temperature elevation time was short and the vapor generation quantities in 10 minutes and in 20 minutes were larger in any of Examples 1 to 4. Also, as is clear from the quantity of coating the thickness of the exothermic layer was able to be increased.

On the contrary, since the content of water contained in the water-retention sheet was 38 mass % of the maximum water absorption of the water-retention sheet in Comparative Example 1, the rate of temperature elevation was lower and moreover, the vapor generation quantity in 20 minutes was smaller. Further, the thickness of the exothermic layer was also increased.

TABLE 1

| BLENDING QUANTITY (PARTS BY MASS) | Example 1 | Example 2 | Example 3 | Example 4 | Comparative Example 1 |
|---|---|---|---|---|---|
| OXIDIZEABLE METAL (IRON POWDER) | 100 | 100 | 100 | 100 | 100 |
| WATER-RETENTION AGENT (ACTIVATED CARBON) | 4 | 4 | 8 | 12 | 4 |
| WATER | 50 | 50 | 62 | 72 | 50 |
| REACTION ACCELERATOR AGENT (SODIUM | 5 | 5 | 5 | 5 | 5 |
| THICKENING AGENT (XANTHAN GUM) | 0.25 | 0.25 | 0.25 | 0.25 | 0.25 |

TABLE 1-continued

| BLENDING QUANTITY (PARTS BY MASS) | Example 1 | Example 2 | Example 3 | Example 4 | Comparative Example 1 |
|---|---|---|---|---|---|
| QUANTITY OF COATING (g) | 1.65 | 4.04 | 2.43 | 3.23 | 4.26 |
| GRAMMAGE OF IRON POWDER (g/m$^2$) | 414.4 | 1014.5 | 554.6 | 682.7 | 1070.8 |
| GRAMMAGE OF WATER-RETENTION AGENT (g/m$^2$) | 16.58 | 40.58 | 44.37 | 81.92 | 42.83 |
| (A) WATER CONTENT OF HEATING IMPLEMENT ENTIRE (PARTS BY MASS FOR 100 PARTS BY MASS OF THE OXIDIZEABLE METAL) | 50 | 50 | 62 | 72 | 63.8 |
| WATER-RETENTION AGENT IN EXOTHERMIC LAYER (mass %) | 2 | 2 | 5 | 6 | 2 |
| WATER PERCENTAGE IN EXOTHERMIC LAYER (%) | 7.9 | 15.8 | 14.5 | 23.8 | 21.86 |
| (C) WATER CONTENT IN EXOTHERMIC LAYER (PARTS BY MASS FOR 100 PARTS BY MASS OF THE OXIDIZEABLE METAL) | 8.9 | 20.9 | 19.5 | 37.2 | 31.6 |
| WATER CONTENT OF WATER-RETENTION SHEET (g) | 0.42 | 0.73 | 0.59 | 0.59 | 0.92 |
| MAXIMUM WATER ABSORPTION OF WATER RETENTION SHEET (g) | 2.44 | 2.44 | 2.44 | 2.44 | 2.44 |
| (D) WATER CONTENT OF WATER-RETENTION SHEET/ MAXIMUM WATER ABSORPTION OF WATER-RETENTION SHEET (%) | 17.2 | 30.0 | 24.2 | 24.2 | 37.8 |
| (E) AIR RESISTANCE OF WATER-RETENTION SHEET (second/100 ml) | 2 | 2 | 2 | 2 | 2 |
| GRAMMAGE OF WATER IN WATER-RETENTION SHEET (g/m$^2$) | 168 | 292 | 236 | 236 | 368 |
| AIR RESISTANCE OF FIRST BAG-FIRST SHEET | 2,500 | 2,500 | 2,500 | 2,500 | 2,500 |
| AIR RESISTANCE OF FIRST BAG-SECOND SHEET (second/100 ml) | NON-AIR PERMEABLE | NON-AIR PERMEABLE | NON-AIR PERMEABLE | NON-AIR PERMEABLE | NON-AIR PERMEABLE |
| EXOTHERMIC CHARACTERISTICS | | | | | |
| MAXIMUM TEMPERATURE (DEGREES C.) | 53.2 | 69.1 | 66.8 | 67.4 | 69.2 |
| 35 → 45 DEGREES C. TEMPERATURE ELEVATION TIME (minute) | 2 | 5 | 1.9 | 2 | 15.2 |
| VAPOR QUANTITY IN 10 MINUTES (mg) | 88 | 59.8 | 145.7 | 173.4 | 32.2 |
| VAPOR QUANTITY IN 20 MINUTES (mg) | 149.6 | 170.3 | 272.7 | 433.6 | 71.7 |

The invention claimed is:

1. A vapor heating implement, comprising:
   an exothermic layer;
   a water-retention layer; and
   a bag containing the exothermic layer and the water-retention layer;
   wherein:
   the exothermic layer comprises an oxidizable metal, water, and a water-retention agent;
   the water-retention layer comprises a polymer;
   the bag is at least partially air permeable;
   a content of water in the vapor heating implement is 40 to 80 parts by mass per 100 parts by mass of the oxidizable metal;
   a content of the water-retention agent in the exothermic layer is 0.3 to 20 parts by mass per 100 parts by mass of the oxidizable metal;
   a content of water in the exothermic layer is 8 to 45 parts by mass per 100 parts by mass of the oxidizable metal; and
   a content of water in the water-retention layer is 15 to 30 mass % of a maximum water absorption of the water-retention sheet.

2. The vapor heating implement according to claim 1, wherein:
   the water-retention agent comprises a carbon component; and
   a content of the carbon component in the water-retention agent at least 90 mass %.

3. The vapor heating implement according to claim 1, wherein the exothermic layer and the water-retention layer are arranged in the bag so that the water-retention layer is closer to a skin surface of a user when the vapor heating implement is in use.

4. The vapor heating implement according to claim 1, wherein:
   the vapor heating implement comprises a sheet provided inside the bag and on a side of the exothermic layer opposite from the water-retention layer; and
   the sheet has an air resistance having a value of at least 50,000 seconds/100 ml.

5. The vapor heating implement according to claim 1, wherein the water-retention layer has an air resistance having a value of 500 seconds/100 ml or less.

6. The vapor heating implement according to claim 1, wherein:
   the bag comprises a first sheet and a second sheet enclosing the exothermic layer and the water-retention layer;
   the first sheet is provided on a side of the exothermic layer and the water-retention layer closer to a skin surface of a user when the vapor heating implement is in use, and the second sheet is provided on a side of the exothermic layer and the water-retention layer away from the skin surface of the user when the vapor heating implement is in use; and
   the first sheet has an air resistance having a value of 1,000 to 7,000 seconds/100 ml.

7. The vapor heating implement according to claim 1, wherein:
   the bag comprises a first sheet and a second sheet enclosing the exothermic layer and the water-retention layer;
   the first sheet is provided on a side of the exothermic layer and the water-retention layer closer to a skin surface of a user when the vapor heating implement is in use, and the second sheet is provided on a side of the exothermic layer and the water-retention layer away from the skin surface of the user when the vapor heating implement is in use; and the second sheet an air resistance value of at least 50,000 seconds/100 ml.

8. The vapor heating implement according to claim 1, wherein the content of water in said water-retention layer, in grammage, is 50 to 350 g/m$^2$.

9. The vapor heating implement according to claim 1, wherein the water-retention layer comprises a fiber-based material and a water-absorbing polymer.

10. The vapor heating implement according to claim 1, wherein the exothermic layer comprises a polysaccharide-based thickening agent having a molecular weight of 1,000,000 to 50,000,000.

11. The vapor heating implement according to claim 10, wherein a content of the polysaccharide-based thickening agent is 0.05 to 5 parts by mass per 100 parts by mass of the oxidizable metal.

12. The vapor heating implement according to claim 1, wherein the water-retention agent comprises at least one of a carbon component, a fiber material, a water-absorbing polymer, and a water-absorbing powder.

13. The vapor heating implement according to claim 1, wherein:
the water-retention agent comprises a carbon component; and
a mean particle diameter of the carbon component is 10 to 200 μm.

14. The vapor heating implement according to claim 3, wherein:
the bag comprises a first sheet and a second sheet enclosing the exothermic layer and the water-retention layer;
the first sheet is provided on a side of the exothermic layer and the water-retention layer closer to the skin surface of the user when the vapor heating implement is in use, and the second sheet is provided on a side of the exothermic layer and the water-retention layer away from the skin surface of the user when the vapor heating implement is in use;
the first sheet has an air resistance having a value of 1,000 to 7,000 seconds/100 ml; and
the second sheet an air resistance value of at least 50,000 seconds/100 ml.

15. The vapor heating implement according to claim 14, wherein:
the vapor heating implement comprises a third sheet provided inside the bag and on a side of the exothermic layer opposite from the water-retention layer; and
the third sheet has an air resistance having a value of at least 50,000 seconds/100 ml.

16. An eye mask, comprising:
an elongate main body portion;
a first ear hook portion comprising a first opening configured to accommodate a user's first ear, the first ear hook portion extending from a first end of the elongate main body portion; and
a second ear hook portion comprising a second opening configured to accommodate the user's second ear, the second ear hook portion extending from a second end of the elongate main body;
wherein the main body portion comprises the vapor heating implement of claim 1.

17. An eye mask, comprising:
an elongate main body portion;
a first ear hook portion comprising a first opening configured to accommodate a user's first ear, the first ear hook portion extending from a first end of the elongate main body portion; and
a second ear hook portion comprising a second opening configured to accommodate the user's second ear, the second ear hook portion extending from a second end of the elongate main body;
wherein the main body portion comprises the vapor heating implement of claim 3.

18. An eye mask, comprising:
an elongate main body portion;
a first ear hook portion comprising a first opening configured to accommodate a user's first ear, the first ear hook portion extending from a first end of the elongate main body portion; and
a second ear hook portion comprising a second opening configured to accommodate the user's second ear, the second ear hook portion extending from a second end of the elongate main body;
wherein the main body portion comprises the vapor heating implement of claim 14.

19. An eye mask, comprising:
an elongate main body portion;
a first ear hook portion comprising a first opening configured to accommodate a user's first ear, the first ear hook portion extending from a first end of the elongate main body portion; and
a second ear hook portion comprising a second opening configured to accommodate the user's second ear, the second ear hook portion extending from a second end of the elongate main body;
wherein the main body portion comprises the vapor heating implement of claim 15.

* * * * *